(12) United States Patent
Phipps et al.

(10) Patent No.: US 6,355,025 B1
(45) Date of Patent: Mar. 12, 2002

(54) ADJUSTABLE ELECTROTRANSPORT DRUG DELIVERY USING A FIXED OUTPUT CONTROLLER

(75) Inventors: J. Bradley Phipps, Plymouth; Gary A. Lattin, Forest Lake, both of MN (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 08/485,960

(22) Filed: Jun. 7, 1995

(51) Int. Cl.[7] .................................................. A61N 1/30
(52) U.S. Cl. ........................................ 604/501; 604/20
(58) Field of Search .............................. 604/20–21, 501; 607/115, 149, 152–153

(56) References Cited

U.S. PATENT DOCUMENTS

| | | | |
|---|---|---|---|
| 4,141,359 A | 2/1979 | Jacobsen et al. | 128/172.1 |
| 4,416,274 A | 11/1983 | Jacobsen et al. | 604/20 |
| 4,722,726 A | 2/1988 | Sanderson et al. | 604/20 |
| 5,006,108 A | 4/1991 | LaPrade | 604/20 |
| 5,023,085 A | 6/1991 | Francoeur et al. | 424/449 |
| 5,047,007 A | 9/1991 | McNichols et al. | 604/20 |
| 5,125,894 A * | 6/1992 | Phipps et al. | |
| 5,135,477 A | 8/1992 | Untereker et al. | 604/20 |
| 5,135,479 A * | 8/1992 | Sibalis et al. | |
| 5,135,480 A * | 8/1992 | Bannon et al. | |
| 5,224,927 A * | 7/1993 | Tapper | |
| 5,224,928 A | 7/1993 | Sibalis et al. | 604/20 |
| 5,246,418 A | 9/1993 | Haynes et al. | 604/20 |
| 5,250,022 A * | 10/1993 | Chien et al. | |
| 5,254,081 A | 10/1993 | Maurer et al. | 604/20 |
| 5,320,597 A | 6/1994 | Sage, Jr. et al. | 604/20 |
| 5,358,483 A | 10/1994 | Sibalis | 604/20 |

FOREIGN PATENT DOCUMENTS

| | | | |
|---|---|---|---|
| GB | 2239803 A | 7/1991 | A61N/1/30 |

OTHER PUBLICATIONS

U.S. application No. 08/410,112, Lattin et al., filed Mar 24, 1995.

* cited by examiner

Primary Examiner—Mark Bockelman
(74) Attorney, Agent, or Firm—D. Byron Miller; Owen J. Bates

(57) ABSTRACT

The invention provides a method for adjusting, i.e., varying, the rate of delivery of a therapeutic agent through a body surface from an electrotransport assembly of the type which includes a predetermined, e.g., fixed, output electronic controller and a detachable therapeutic agent source. The method provides a plurality of therapeutic agent sources in which a single parameter or a series of parameters has been varied. The plurality of agent sources are supplied, one at a time, to the controller of the electrotransport assembly, so that together (i.e., source and controller) the agent delivery rate is varied.

28 Claims, 2 Drawing Sheets

ADJUSTABLE ELECTROTRANSPORT DRUG DELIVERY USING A FIXED OUTPUT CONTROLLER

TECHNICAL FIELD

The present invention relates to delivery of therapeutic agents through a body surface by electrotransport. More particularly, the invention relates to a method of varying the drug delivery rate from an electrotransport device utilizing a two-part electrotransport delivery device comprised of an electronic controller adapted to be coupled to, one at a time, a plurality of therapeutic agent (e.g., drug) containing units.

BACKGROUND ART

The transdermal delivery of drugs, by diffusion through the epidermis, offers improvements over more traditional delivery methods, such as subcutaneous injections and oral delivery. Transdermal drug delivery avoids the hepatic first pass effect encountered with oral drug delivery. Transdermal drug delivery also eliminates patient discomfort associated with subcutaneous injections. In addition, transdermal delivery can provide more uniform concentrations of drug in the bloodstream of the patient over time due to the extended controlled delivery profiles of certain types of transdermal delivery devices. The term "transdermal" delivery, broadly encompasses the delivery of an agent through a body surface, such as the skin, mucosa, or nails of an animal.

The skin functions as the primary barrier to the transdermal penetration of materials into the body and represents the body's major resistance to the transdermal delivery of therapeutic agents such as drugs. To date, efforts have been focussed on reducing the physical resistance or enhancing the permeability of the skin for the delivery of drug by passive diffusion. Various methods for increasing the rate of transdermal drug flux have been attempted, most notably using chemical flux enhancers.

Other approaches to increase the rates of transdermal drug delivery include use of alternative energy sources such as electrical energy and ultrasonic energy. Electrically assisted transdermal delivery is also referred to as electrotransport. The term "electrotransport" as used herein refers generally to the delivery of an agent (e.g., a drug) through a membrane, such as skin, mucous membrane, or nails. The delivery is induced or aided by application of an electrical potential. For example, a beneficial therapeutic agent may be introduced into the systemic circulation of a human body by electrotransport delivery through the skin.

A widely used electrotransport process, electromigration (also called iontophoresis), involves the electrically induced transport of charged ions. Another type of electrotransport, electroosmosis, involves the flow of a liquid, which liquid contains the agent to be delivered, under the influence of an electric field. Still another type of electrotransport process, electroporation, involves the formation of transiently-existing pores in a biological membrane by the application of an electric field. An agent can be delivered through the pores either passively (i.e., without electrical assistance) or actively (i.e., under the influence of an electric potential). However, in any given electrotransport process, more than one of these processes, including at least some "passive" diffusion, may be occurring simultaneously to a certain extent. Accordingly, the term "electrotransport", as used herein, should be given its broadest possible interpretation so that it includes the electrically induced or enhanced transport of at least one agent, which may be charged, uncharged, or a mixture thereof, whatever the specific mechanism or mechanisms by which the agent actually is transported.

Electrotransport devices use at least two electrodes that are in electrical contact with some portion of the skin, nails, mucous membrane, or other surface of the body. One electrode, commonly called the "donor" electrode, is the electrode from which the agent is delivered into the body. The other electrode, typically termed the "counter" electrode, serves to close the electrical circuit through the body. For example, if the agent to be delivered is positively charged, i.e., a cation, then the anode is the donor electrode, while the cathode is the counter electrode which serves to complete the circuit. Alternatively, if an agent is negatively charged, i.e., an anion, the cathode is the donor electrode and the anode is the counter electrode. Additionally, both the anode and cathode may be considered donor electrodes if both anionic and cationic agent ions, or if uncharged dissolved agents, are to be delivered.

Electrotransport delivery systems additionally require at least one reservoir or source of the agent to be delivered to the body, i.e., donor reservoirs. Such donor reservoirs are electrically connected to, and positioned between, the anode or cathode and the body surface, to provide a fixed or renewable source of one or more agents or drugs. Examples of such donor reservoirs include a pouch or cavity, a porous sponge or pad, and a hydrophilic polymer or a gel, particularly a hydrogel, matrix. Hydrogels have become particularly favored for use as the drug and electrolyte reservoir matrices, in part, due to their high equilibrium water content and their ability to quickly absorb water. In addition, hydrogels tend to have good biocompatibility with the skin and with mucosal membranes.

Electrotransport devices also have an electrical power source such as one or more batteries. Typically at any one time, one pole of the power source is electrically connected to the donor electrode, while the opposite pole is electrically connected to the counter electrode. Since it has been shown that the rate of electrotransport drug delivery is approximately proportional to the electric current applied by the device, many electrotransport devices typically have an electrical controller that controls the voltage and/or current applied through the electrodes, thereby regulating the rate of drug delivery. These control circuits use a variety of electrical components to control the amplitude, polarity, timing, waveform shape, etc. of the electric current and/or voltage supplied by the power source. See, for example, McNichols et al., U.S. Pat. No. 5,047,007.

To date, commercial transdermal electrotransport drug delivery devices (e.g., the Phoresor, sold by Iomed, Inc. of Salt Lake City, Utah; the Dupel Iontophoresis System sold by Empi, Inc. of St. Paul, Minn; the Webster Sweat Inducer, model 3600, sold by Wescor, Inc. of Logan, Utah) have generally utilized a desk-top electrical power supply unit and a pair of skin contacting electrodes. The donor electrode contains a drug solution while the counter electrode contains a solution of a biocompatible electrolyte salt. The power supply unit has electrical controls for adjusting the amount of electrical current applied through the electrodes. The "satellite" electrodes are connected to the electrical power supply unit by long (e.g., 1–2 meters) electrically conductive wires or cables. The wire connections are subject to disconnection and limit the patient's movement and mobility. Wires between electrodes and controls may also be annoying or uncomfortable to the patient. Other examples of desk-top electrical power supply units which use "satellite" electrode assemblies are disclosed in Jacobsen et al., U.S. Pat. No. 4,141,359 (see FIGS. 3 and 4); LaPrade, U.S. Pat. No. 5,006,108 (see FIG. 9); and Maurer et al., U.S. Pat. No. 5,254,081.

More recently, small self-contained electrotransport delivery devices have been proposed to be worn on the skin, sometimes unobtrusively under clothing, for extended periods of time. Such small self-contained electrotransport delivery devices are disclosed, for example, in Tapper, U.S. Pat. No. 5,224,927; Sibalis, et al., U.S. Pat. No. 5,224,928; and Haynes et al., U.S. Pat. No. 5,246,418.

There have recently been suggestions to utilize electrotransport devices having a reusable controller which is adapted for use with multiple drug-containing units. The drug-containing units are simply disconnected from the controller when the drug becomes depleted and a fresh drug-containing unit is thereafter connected to the controller. In this way, the relatively more expensive hardware components of the device (e.g., batteries, LED's, circuit hardware, etc.) can be contained within the reusable controller, and the relatively less expensive donor reservoir and counter reservoir matrices can be contained in the single use/disposable drug-containing unit, thereby bringing down the overall cost of electrotransport drug delivery.

Examples of electrotransport devices comprised of a reusable controller, removably connected to a drug-containing unit are disclosed in Sage, Jr. et al., U.S. Pat. Nos. 5,320,597; Sibalis, 5,358,483; Sibalis et al., U.S. Pat. No. 5,135,479 (FIG. 12); and Devane et al., UK Patent Application 2 239 803. The Devane Application discloses a two-part electrotransport system comprised of a controller and a drug-containing unit. The two parts are electrically and mechanically coupled to form a complete electrotransport device. One of the Devane devices has cooperating electrical contacts on the controller and drug unit; specifically, projections on the drug unit engage microswitches on the controller, to select a given therapeutic program/electrotransport current. Another of the Devane electrotransport devices has a bar code on the drug unit which can presumably be scanned by a scanner in the controller (eg, by passing the scanner over the bar code) to signal the controller the type of drug-containing unit that is being connected thereto.

Of particular interest in transdermal delivery utilizing electrotransport systems is the ability to alter the rate of drug delivery, as many medical situations warrant variation in the rate of delivery. Variation in the rate of drug delivery in an electrotransport system achieves a critically important objective, i.e., dosage control. It is known that the electrotransport drug delivery rate (in mg/h) can be increased (or decreased) by (1) increasing (or decreasing) the concentration of the drug in the donor reservoir; (2) increasing (or decreasing) the skin contact area of the donor reservoir; (3) increasing (or decreasing) the applied electrotransport current density; and/or (4) decreasing (or increasing) the concentration of competitive co-ions (i.e., ions other than the drug ions which have the same polarity as the drug ions and which are co-delivered with the drug into the body by electrotransport) in the donor reservoir.

Further, as described above, because the rate of electrotransport drug delivery is approximately proportional to the electric current applied by the electrotransport device, many electrotransport devices have a variable output electrical controller. In a variable output controller, the voltage and/or current applied through the electrodes can be varied, and in this manner, the rate of drug delivery is regulated. Typically, the adjustment of the controller requires trained personnel who can adjust the current and/or voltage output of the controller in order to achieve a particular drug delivery rate. Thus, when an adjustment in drug delivery is medically warranted (i.e., when a change of dosage is desired), the need to reset the output of the controller makes such systems unduly expensive, e.g., in terms of personnel costs, and are not at all suited for dosing adjustments to be made in the hands of untrained personnel, e.g., by the patients.

Despite recognition of these various aspects of drug delivery, the prior art has produced very little in the way of a simple technique for allowing untrained personnel, such as patients, to vary the rate of electrotransport drug delivery.

DISCLOSURE OF THE INVENTION

The present invention provides an improved and simplified method of varying the rate of drug delivery from an electrotransport device. As such, the method provides a greater degree of efficiency and control in electrotransport delivery of therapeutic agents, concomitantly providing a greater measure of therapeutic efficacy and patient safety.

The foregoing, and other advantages of the present invention, are realized in one aspect thereof in a method for varying drug delivery rate of a therapeutic agent through a body surface from an electrotransport assembly of the type which includes an electronic controller component and a detachable drug-containing unit. The drug-containing unit includes an active electrode. The controller component operates at a fixed or at a substantially fixed electrical output, as defined hereinafter. The method includes providing, one at a time, a plurality of classes of drug-containing units, each class of drug-containing units having a specific dose different from the other classes. Changes in drug delivery rate are preferably accomplished by changing the class of drug-containing units rather than changing the output of the controller of the electrotransport assembly. The specific doses of each class of drug-containing unit are formulated in a variety of manners, including varying, from class to class, the drug or agent concentration, the competitive co-ion content, the donor reservoir skin contact area, physical properties (e.g., drug-polymer interaction), and chemical properties (e.g., pH, solvent composition, enhancers). Each variation or a combination of these variations suitably produces a different class of drug-containing units which effectively delivers a specific predetermined drug dose.

Other advantages and a fuller appreciation of the specific attributes of this invention will be gained upon an examination of the following drawings, detailed description of preferred embodiments, and appended claims. It is expressly understood that the drawings are for the purpose of illustration and description only, and are not intended as a definition of the limits of the invention.

BRIEF DESCRIPTION OF THE DRAWINGS

For a further understanding of the objects and advantages of the present invention, reference is made to the following detailed description, taken in conjunction with the accompanying drawings, in which like parts are given like reference numerals and wherein.

MODES FOR CARRYING OUT THE INVENTION

Figure 1:
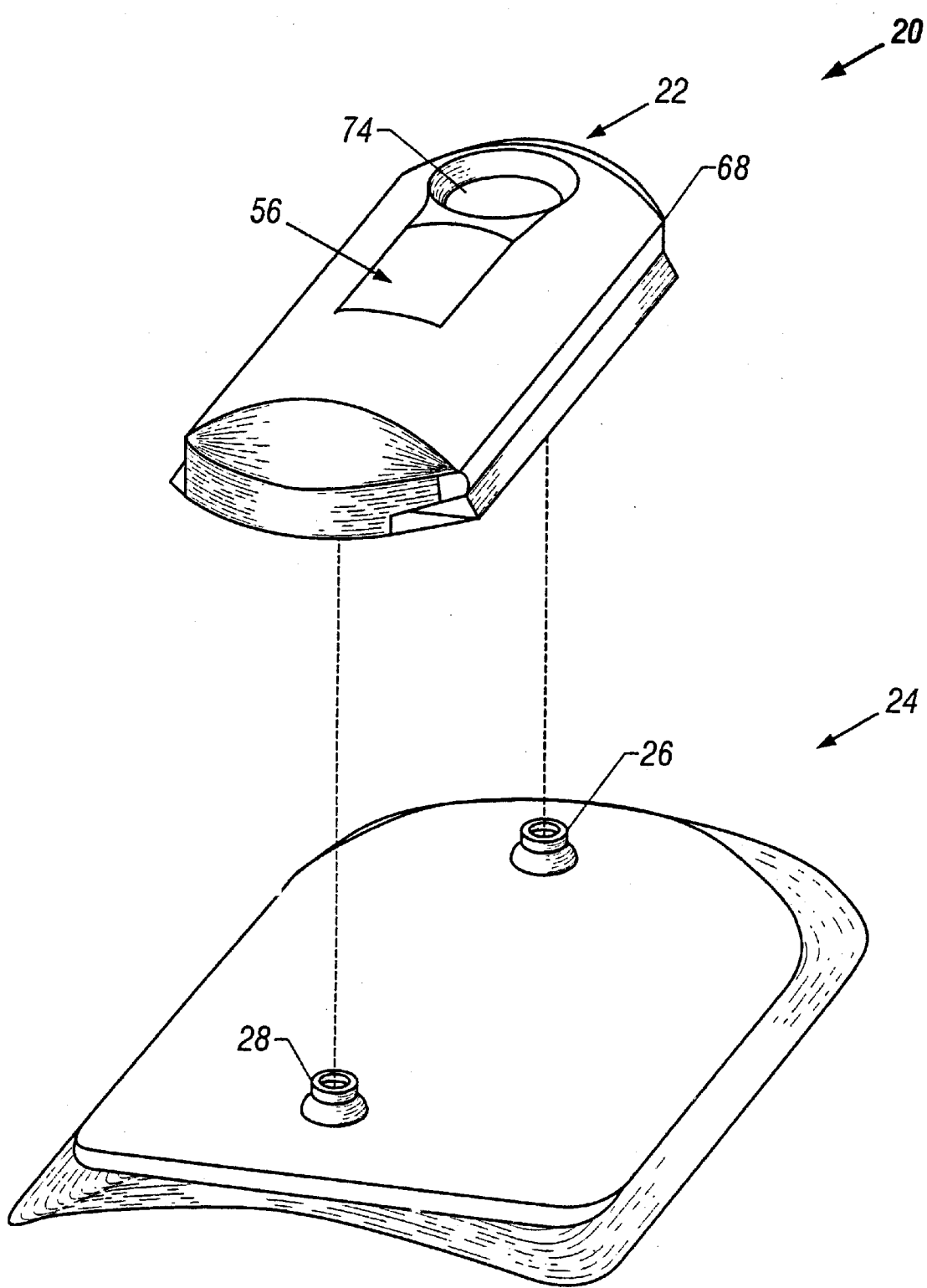
FIG. 1 is a perspective view of an exemplary electrotransport device in accordance with the present invention.

The present invention relates broadly to an improved electrotransport system and to improved methods for electrotransport delivery of therapeutic agents. More specifically, the present invention provides a simple and efficient method for altering electrotransport drug delivery rate. Accordingly, the present invention will now be described in detail with respect to such endeavors; however, those skilled in the art will appreciate that the following description of the invention is meant to be exemplary only and should not be viewed as limitative on the full scope thereof.

The present invention is characterized by an ability to vary drug delivery rate utilizing a fixed or substantially fixed output electronic controller and multiple drug-containing units in an electrotransport system. The system permits a physician to alter drug dosages for a patient without the need to replace the controller or reset the electrical (i.e. current and/or voltage) output of the controller. Instead, the physician simply prescribes a new class of drug-containing units for use with the same controller. In this manner, the controller output can be set or programmed at the factory or by a pharmacist, e.g., when the controller is first dispensed. The system provides less expensive electrotransport drug delivery regimens because (1) the controller has no patient adjustable electric current/voltage output features, and (2) the controller is reusable, i.e., it is adapted to be used with a plurality of similar or different drug-containing units. Adjusting the drug delivery (i.e., dosing) rates is achieved through a novel combination of physical and chemical features.

In the following description of the method of the invention, process steps are carried out at room temperature and atmospheric pressure unless otherwise specified. As used herein, the terms "fixed output", "predetermined output" or "preprogrammed output" refer to a current/voltage output of an electronic controller of an electrotransport assembly or device which is determined at the factory (or by a pharmacist), but cannot be readily altered by the patient or care provider. The "fixed output" can mean an electric current and/or voltage output which is constant (e.g., a constant DC current output) or one that is time-varying (e.g., a pulsatile DC current, or other current which varies over the time of application) but is preprogrammed to perform in a single, fixed manner. The term "transdermal" is meant to be interpreted broadly to refer to drug delivery across any body surface or membrane, including skin.

The present invention includes a single and, e.g., a reusable, fixed or substantially fixed output electronic controller which is universally mated to a number of different drug-containing units having a donor reservoir, thereby achieving different drug delivery rates, without adjusting the controller output. In general, the drug units have a much more limited life than the controller. Most typically, the drug units have an operational life span measured in hours (e.g., 1 to 100 hours) whereas the controller has a life span measured in weeks or months (e.g., 1 to 100 weeks). At the end of the operational life span of the drug unit (e.g., when the drug contained therein has become depleted), the drug unit is disconnected from the controller and a new drug unit is connected in its place. Each class of drug-containing units has a donor reservoir with a different composition or formulation designed to provide a specific dose of a drug or therapeutic agent. Changing the composition or formulation of the donor reservoir varies the rate of electrotransport drug delivery, since the electrical output of the controller is fixed or substantially fixed. The drug delivery rate is, thus, determined by the composition or formulation of the donor reservoir of the drug unit, and not necessarily by the current/voltage output of the controller component, although both strategies in combination are contemplated within the scope of the invention.

In a preferred embodiment, the method of the present invention is suitably performed using an electrically powered transdermal electrotransport device that includes a reusable electronic controller which is adapted for use with multiple single use drug-containing units. The reusable controller suitably includes the power source of the device, e.g., batteries, circuit hardware and LED, i.e., the hardware components of the device. The controller component of the present invention suitably has a fixed or substantially fixed output, e.g., a preprogrammed current or voltage output.

The single use drug-containing unit includes an active or donor electrode assembly. The active electrode assembly includes an active electrode and a drug or therapeutic agent to be delivered contained in a donor reservoir, e.g., a hydrogel. Optionally, the drug-containing unit includes two electrodes, i.e., both a cathode and an anode. Most preferably, the drug-containing unit includes two electrodes, each electrode being in electrical contact with a reservoir, one reservoir being the donor reservoir containing the drug to be delivered, the other reservoir being a counter reservoir containing a biocompatible electrolyte.

In operation, the drug dose administered by the electrotransport system is altered by use of a drug-containing unit having an appropriate drug reservoir composition designed to give a specific dose. In other words, when the dosing rate needs to be changed, the drug-containing unit which is presently in use is disconnected from the controller and replaced with a new drug-containing unit having a different composition. Thus, a plurality of drug-containing units are suitably used with a single controller to provide a variation in drug delivery rate. Each different class of drug-containing units is provided with a different drug reservoir composition that is suitably designed to give a specific dose.

Several methods of providing a specific dose of a drug or therapeutic agent in combination with a fixed or substantially fixed output controller in an electrotransport system are within the scope of the present invention. In other words, there are several methods of providing a plurality of classes of drug-containing units useable with the fixed or substantially fixed output controller in which each unit class provides a specific dose of agent or drug. Such methods, described in detail below, use drug-containing units that include a drug reservoir, which is preferably a hydrogel matrix, with the drug (or drug solution) uniformly dispersed therein. The type and quantity of gel matrix ingredients are varied to give a variety of delivery rates for a specific drug concentration and current regimen. Essentially any physiologically and chemically compatible matrix material can be utilized which holds drug or agent in solution or suspension and which does not itself interfere with the electrotransport process. For example, various hydrogel compositions can differ in the loading or concentration of drug, the loading or concentration of competitive co-ions, the donor reservoir skin contact area, physical properties (e.g., drug-polymer interaction), and other chemical properties (e.g., pH, solvent composition, enhancers). Each variation or a combination of these variations can be used to suitably produce a different specific drug dose.

Hydrogels in accordance with the present invention are selected from of variety of nonionic, ionic or polar, synthetic or naturally occurring polymeric materials. Such polymeric materials include, but are not limited to, polyacrylamide, poly(2-hydroxyethyl acrylate), poly(2-hydroxypropyl acrylate), poly(N-vinyl-2-pyrrolidone), poly(n-methylol acrylamide), poly(diacentone acrylamide), poly(2-hydroxyethyl methacrylate), polyvinylalcohol, polyallylalcohol, polyesters, polycarbonates, polyurethanes, polycarboxylates, polysulfonates, poly phosphates, polyamines, cellulose ethers, methyl cellulose ethers, cellulose and hydroxylated cellulose, methyl cellulose, hydroxylated methyl cellulose, gums such as guar, locust, karaya, xanthan, gelatin and derivatives thereof.

Specifically, in one method, for a specific drug concentration, the pH of the gel matrix of the drug reservoir is suitably adjusted to give different delivery rates. For a drug cation, the skin is more cation-selective at higher pH. Thus, as the pH of the matrix increases, the delivery of drug cation increases, i.e., drug flux increases at a specific drug content and current. Similarly, other chemical and physical properties, such as the viscosity or drug absorptive properties of the gel matrix, can be adjusted to give a variety of delivery rates of the same drug content.

A second method for providing specific dosages for each of a plurality of drug-containing units relies on altering the skin contact area of the donor reservoirs. In this method, the drug unit preferably includes both a drug-containing donor reservoir and an electrolyte-containing counter reservoir, most preferably formed of gel matrices. The donor reservoir is segmented into a plurality of donor reservoir segments, each segment preferably having the same size and volume. See, e.g., Untereker et al., U.S. Pat. No. 5,135,477 and Jacobsen et al., U.S. Pat. No. 4,416,274, the disclosures of which are incorporated by reference herein. Some of the reservoir segments are loaded with drug, while others are drug-free, containing only a biocompatible electrolyte (e.g., NaCl). At a constant current regimen, the drug delivery rate for drug-containing units in accordance with this embodiment of the present invention is regulated by varying the ratio of drug-loaded to drug-free reservoir segments in contact with the active electrode. For example, to increase the rate, the ratio of drug-loaded to drug-free donor reservoir segments is increased. In effect, drug delivery rate differences are achieved by altering the relative skin contact area of the drug-containing reservoir segments while maintaining a constant overall current density.

A third method involves intentionally adding, or intentionally generating during electrotransport drug delivery, competitive co-ions to the drug-containing reservoir. Competitive co-ions are ions having the same charge as the drug being delivered and which compete with the drug for "carrying" the applied electrotransport current. Thus, for a drug-containing donor reservoir of a particular size and composition, at any predetermined applied electrotransport current, the electrotransport drug delivery rate can be (1) increased by reducing the number of competing co-ions, or (2) decreased by increasing the number of competing co-ions in the donor reservoir. Thus, the drug delivery rate is determined by varying the concentration ratio of drug ion to co-ion. For example, a decrease in the drug ion to co-ion ratio results in a decrease in the drug flux at a specific drug content and current. In use of this method, over time, a depletion of the competitive co-ion can occur, resulting in an increase in drug flux for a given current. Such an effect can be minimized by selecting for use co-ions whose mobility closely matches the mobility of the drug ion through the body surface. Alternatively, the controller is suitably preprogrammed to reduce the current output with time to compensate for an increase in drug flux due to the preferential loss of the competitive co-ion.

Use of competitive co-ions can also be affected by the inclusion of a secondary electrode in the drug reservoir which generates competitive co-ions to replace those delivered from the donor reservoir into the patient. One example of such a secondary electrode, and its method of operation, can be found in Phipps et al. U.S. Pat. No. 5,125,894, the disclosures of which are incorporated herein by reference.

A fourth method involves altering the drug concentration of the drug reservoir to alter the drug flux at a specific current. Over time, however, the drug concentration decreases. Thus, in this embodiment, the controller is preprogrammed to increase the current output as the drug is depleted, thereby compensating for the decreasing drug concentration.

A fifth method involves altering the composition of the solvent phase of the drug-containing reservoir. When the drug delivery via transdermal electrotransport is primarily due to electromigration of ionic drug species, then the degree of ionization can be used to alter the drug flux. The degree of ionization can be controlled by the solvent pH and/or by the ion solvating properties of the solvent. For example, drugs having acidic substituents become more negatively charged as the pH is increased and drugs having basic substituents become more positively charged as the pH is decreased. The polarity of the solvent can also be altered by mixing water with less ion-solvating ingredients (i.e., cosolvents) such as alcohols (e.g., ethanol, glycerol, polyethylene glycol). As the ratios of water to cosolvent decreases, the concentration of drug ion will decrease. Thus, for a relatively fixed output controller, drug ion flux is increased or decreased by altering solvent composition.

A sixth method involves altering the composition of the drug-containing reservoir by addition of skin penetration enhancers (e.g., oleic acid, glycerol monolaurate, dodecanol). The type or concentration of the penetration enhancer in the drug-containing reservoir can be altered to change the drug delivery rate for a given current/voltage output by the controller. Permeation enhancers are disclosed in U.S. Pat. No. 4,722,726 issued to Sanderson et al. and U.S. Pat. No. 5,023,085 issued to Francoeur et al., the disclosures of which are incorporated by reference herein.

Figure 2:
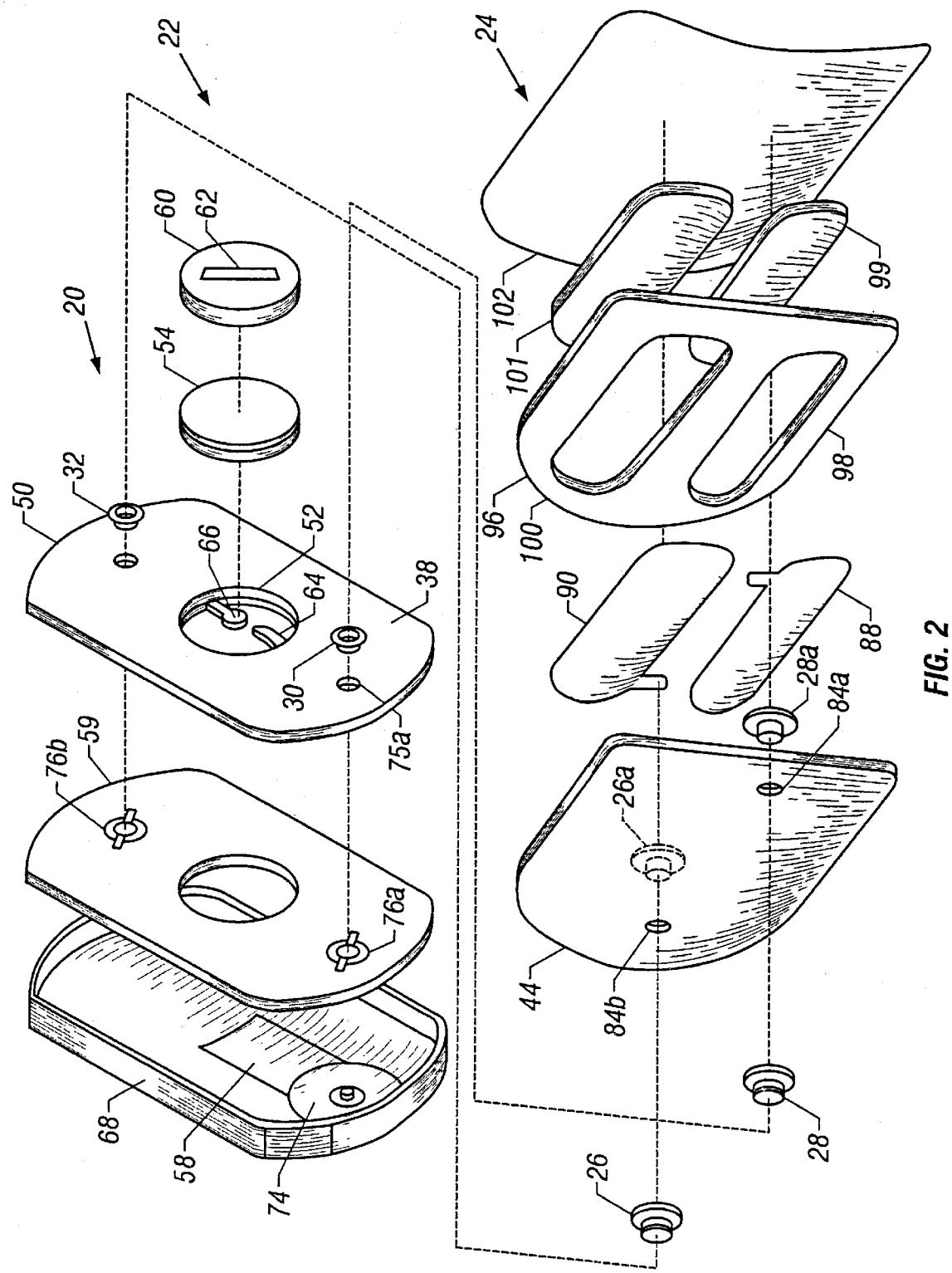
FIG. 2 is an exploded view of the device of FIG. 1.

Reference is now made to FIGS. 1 and 2 which depict an exemplary two-part electrotransport device or electrotransport assembly in accordance with the present invention in which a fixed or substantially fixed output controller is utilized and adapted for use, one at a time, with a plurality of drug-containing units or therapeutic agent sources. FIG. 1 is a perspective view of electrotransport device 20 having a reusable electronic controller 22 which is adapted to be coupled to and uncoupled from, drug-containing unit 24. The controller 22 is reusable, i.e., it is adapted to be used with a plurality of drug units 24, e.g., a series of similar and/or very different drug units 24. On the other hand, drug unit 24 typically has a more limited life and is adapted to be discarded after use, i.e., when the drug contained therein has been delivered or has been depleted. Thus, after the drug contained in drug unit 24 becomes depleted after a predetermined operational life (e.g., 24 hours), the drug unit 24 is uncoupled from the controller 22 and replaced with a fresh drug unit 24 of the same or different structure and/or composition. The controller 22 is designed to provide a predetermined electrical output which is preferably set at the time the controller is manufactured. For purposes of illustration, the controller 22 can be designed to be used with two different drug units 24, both of which units are adapted to be used with the same controller 22 to continuously deliver drug over a period of 12 hours. The two different drug units 24 contain the same drug in their respective donor reservoirs but each contains a different amount of the drug. The drug unit 24 which contains a greater amount or concentration of drug is a "high dose" drug unit. The drug unit 24 which contains a lesser amount or concentration of drug is a "low dose" drug unit.

With reference to FIG. 2, there is shown an exploded view of both the drug unit 24 and the controller 22. The controller 22 is comprised of an upper housing 68 and a lower housing 50, both typically formed of a molded plastic such as polypropylene. The upper housing 68 is joined to the lower housing 50 by a contiguous splash proof, and preferably water proof, peripheral seal. The seal can be made by heat sealing or ultrasonic welding of the joint between housings 50, 68, by gluing the housings together at their common joint using a water proof adhesive, and the like. The lower housing 50 has an opening 52 for receiving a battery 54. Battery contacts 64, 66 are provided to make electrical contact with the respective poles of battery 54. A removable cover 60 screws into the opening 52 to retain the battery 54 in place. The cover 60 has a slot 62 for inserting a coin or a screw driver blade to turn the cover 60 and remove it from the opening 52 in order to access (i.e., replace) the battery 54. The controller 22 includes the battery 54, e.g., a button cell battery, for powering the electrical circuit (not shown) on a circuit board 59. The circuit board 59 is formed in a conventional manner, having conductive traces patterned for interconnecting electrical component(s) thereon which control the magnitude, timing, frequency, waveform shape, etc., of the electrical output (e.g., voltage and/or current) of controller 22. The conductive traces on circuit board 59 may be deposited with a conventional silk screen printing process or a conventional solder coated copper plated mask and etch process. The insulating substrate of circuit board 59 may be made of standard FR-4 or the like. Although not critical to the invention, controller 22 includes a push button switch 74 which can be used to start operation of device 10 and a liquid crystal display 56 (FIG. 1) which can display, through window 58 (FIG. 2), system information such as the particular type of drug unit 24 that is coupled to the controller, the dosing level, the elapsed time of current application, the battery strength, etc. A display such as display 56 is disclosed in co-pending, commonly assigned U.S. patent application Ser. No. 08/410,112, the disclosure of which is incorporated herein by reference.

The lower housing 50 is provided with holes 75a, 75b which hold electrically conductive receptacles 30, 32. The receptacles 30, 32 protrude through respective holes 75a, 75b in lower housing 50. The ends of receptacles 30, 32 are held in place in by, and make electrical contact with the outputs of the electronic circuit on circuit board 59, by respective conductive gripping fasteners 76a, 76b.

The drug unit 24 is configured to be removably coupled to the controller 22, with the top of drug unit 24 adjacent to and facing the bottom of the controller 22. The top of drug unit 24 is provided with the male parts of two snap type connectors, the male parts being posts 26 and 28 which extend upwardly from drug unit 24. Receptacle 32 is positioned and sized to receive donor post 26 and receptacle 30 is positioned and sized to receive counter post 28. One snap connector pair, for example, receptacle 30 and post 28, is preferably made larger than the other snap connector pair (i.e., receptacle 32 and post 26) in order to provide a polarity specific connection of the drug unit 24 to the controller 22. Receptacles 30, 32 and posts 26, 28 are made from an electrically conductive material (e.g., a metal such as silver, brass, stainless steel, platinum, gold, nickel, beryllium-copper, etc or a metal coated polymer, e.g., ABS with a silver coating). The donor post 26 is electrically connected to a donor electrode 90, which in turn is electrically connected to a donor reservoir 101 which typically contains a solution of the therapeutic agent (e.g., a drug salt) to be delivered. The counter post 28 is electrically connected to a counter electrode 88, which in turn is electrically connected to a counter reservoir 99 which typically contains a solution of a bio-compatible electrolyte (e.g., buffered saline). The electrodes 88 and 90 are typically comprised of electrically conductive materials, most preferably a silver (e.g., silver foil or silver powder loaded polymer) anodic electrode and a silver chloride cathodic electrode. The reservoirs 99 and 101 typically include hydrogel matrices which hold the drug or electrolyte solutions and are adapted to be placed in contact with the body surface (e.g., skin) of a patient (not shown) when in use. The electrodes 88, 90 and the reservoirs 99, 101 are isolated from each other by a foam member 96. The bottom (i.e., patient contacting) surface of foam member 96 is preferably coated with a skin contact adhesive in order to secure drug unit 24 on the patient's body. A release liner 102 covers the body contacting surfaces of the two reservoirs 99 and 101 and the adhesive coated surface of foam member 96 before the drug unit 24 is put in use. The release liner 102 is preferably a silicone coated polyester sheet. The release liner 102 is removed when the device 20 is applied to the skin of a patient (not shown).

Thus, the post 26 and the receptacle 30 comprise a snap type connector which electrically connects an output 76a of the circuit on circuit board 59 to the electrode 90 and the reservoir 101. Similarly, the post 28 and the receptacle 30 comprise a snap type connector which electrically connects an output 76a of the circuit on circuit board 59 to the electrode 88 and the reservoir 99. In addition to providing the above described electrical connections, the two snap connectors also provide a separable (i.e., not permanent) mechanical connection of the drug unit 24 to the controller 22. Thus, the electrically conductive snap connectors 26, 32 and 28, 30 simultaneously provide the functions of (i) mechanically coupling the drug unit 24 to the connector 22, and (ii) electrically connecting the electrical output of controller 22 to the drug unit 24.

A flexible backing layer 44, which is preferably made of a material (eg, polyethylene sheet) which is impermeable to the passage of liquid water, forms the top-most layer of the drug unit 24. Holes 84a, 84b are provided through the backing layer 44. Conductive base rivets 26a, 28a project through openings 84a, 84b, respectively, and engage the posts 26, 28 to fix the backing layer 44 therebetween.

Electrodes 88, 90 are composed of electrically conductive materials such as a carbon powder/fiber loaded polymer matrix, a metal powder loaded polymer matrix or a metal foil. Electrodes 88, 90 make contact with the base rivets 26a, 28a. A carbon filled or silver particle filled conductive adhesive is used to bond the electrodes 88, 90 to the base rivets 26a, 28a. The electrodes 88, 90 are in electrical contact with reservoirs 99, 101, respectively. An insulating closed cell foam layer 96 has cavities 98, 100 therein, which cavities contain reservoirs 99, 101, respectively. Typically, one of the reservoirs 99, 101 is the donor reservoir which contains a liquid solution of the therapeutic agent to be delivered by electrotransport while the other is the counter reservoir which contains a solution of a bio-compatible electrolyte (eg, saline). The matrix of reservoirs 99, 101 is preferably a gel, e.g., a hydrogel.

The present invention is further explained by the following example which should not be construed by way of limiting the scope of the present invention.

EXAMPLE

In the treatment of chronic pain, the phenomenon of dose-escalation with time to alleviate pain is often experienced by those using narcotic analgesics (e.g., morphine and its analogues, fentanyl and its analogues). This phenomenon requires that dosage be increased over time to achieve an equivalent degree of pain relief. To provide four fentanyl delivery rate units using a single controller preset to apply a current of, e.g., 0.2 mA, four different drug units having the same basic construction but four different fentanyl contents are provided. Each drug unit consists of a medical-grade foam housing with a peripheral adhesive, four hydrogels, each having a skin contact area of 1.0 $cm^2$ contacting a silver anode, and a single 4 $cm^2$ hydrogel containing a biocompatible electrolyte contacting a silver chloride composite cathode. Electrical contact between the controller and the drug unit is made by connection to two snap connectors, one attached to the anode and the other to the cathode. The lowest dosage unit has 1 hydrogel reservoir containing fentanyl, the other three containing biocompatible electrolyte. In order of increasing dosage, the unit has the following reservoirs contents:

2 drug/2 non-drug;

3 drug/1 non-drug; and all 4 drug

Pursuant to medical authorization, the pharmacist then provides a multiple reservoir disposable drug unit to either increase or decrease drug dosage in accordance with the present invention.

In summary, the present invention provides method for adjusting the drug delivery rate from an electrotransport system utilizing a fixed output controller and varying the composition of the drug-containing unit, i.e., the controller is used with a plurality of drug-containing units of differing composition, to provide the variation in drug delivery. The specific dosages of a plurality of drug-containing units is achieved by varying the composition of the units, by, e.g., differing drug concentrations, competitive co-ion concentrations, pH and relative skin contact area of the donor reservoir.

While the present invention has now been described and exemplified with some specificity, those skilled in the art will appreciate the various modifications, including variations, additions, and omissions, that may be made in what has been described. Accordingly, these modifications also are encompassed by the present invention whose scope is defined by the appended claims.

What is claimed is:

1. A method for delivering a therapeutic agent through a body surface, comprising the steps of:

delivering the therapeutic agent through the body surface from an electrotransport assembly of the type which includes a controller component and a detachable therapeutic agent source coupled to the controller component, the controller component operating at a predetermined, fixed electrical output; and adjusting the rate of therapeutic agent delivery by uncoupling the therapeutic agent source from the controller component and coupling each of a plurality of therapeutic agent sources in which a single parameter or a series of parameters has been varied so that agent delivery rate is selectively controllable by coupling and uncoupling said plurality of therapeutic agent sources to the controller component one at a time.

2. The method of claim 1, wherein said single parameter or series of parameters are selected from the group consisting of therapeutic agent concentration, competitive co-ion concentration, skin contact area of therapeutic agent source, pH of therapeutic agent source, pH of solvent of therapeutic agent source, ion solvating property of solvent of therapeutic agent source, and enhancer content, and wherein the electrotransport agent delivery rate from the controller with one of the plurality of therapeutic agent sources is substantially different from the controller with another of said sources.

3. The method of claim 2, wherein the pH of the solvent of the therapeutic agent source is varied.

4. The method of claim 1, wherein each said therapeutic source is a drug reservoir which is a hydrogel having a pH.

5. The method of claim 4, wherein, within said plurality, the pH of the hydrogel is varied.

6. A method for varying drug delivery rate of a therapeutic agent through a body surface, comprising the steps of:

delivering the therapeutic agent through the body surface from an electrotransport assembly of the type which includes an electronic controller component and a detachable drug-containing unit coupled to the controller component, the drug-containing unit having an active electrode, the controller component operating at a fixed output; and uncoupling the drug-containing unit from the controller component and coupling, one at a time, a plurality of drug-containing units to the controller component, each drug-containing unit having a specific dose different from the others of said plurality and coupling and uncoupling said drug-containing unit to the controller component thereby varying drug delivery rate.

7. The method of claim 6, wherein said providing step includes providing drug-containing units comprising multiple reservoirs, each said unit having a first portion of said the reservoirs loaded with drug and a second portion being drug-free, said second portion of reservoirs containing only a biocompatible electrolyte, and wherein the drug delivery rate is varied by varying, within said plurality, the ratio of drug-loaded to drug-free reservoirs in contact with the active electrode.

8. The method of claim 6, wherein said providing step includes providing drug-containing units having a drug and competitive co-ions, and wherein the drug delivery rate is varied by varying, within said plurality, the ratio of drug concentration to co-ion concentration.

9. The method of claim 8, wherein said competitive co-ion concentration is provided by a secondary electrode in the drug-containing unit which generates competitive co-ions.

10. The method of claim 6, wherein said providing step includes providing a plurality of drug-containing units having differing drug concentrations.

11. An electrotransport device for delivering a therapeutic agent through a body surface, the device including a controller which operates at a predetermined, fixed electrical output, the controller being adapted to be detachably connected, one at a time, to a plurality of therapeutic agent sources, the device having:

a plurality of different classes of therapeutic agent sources in which a parameter in each of said different classes has been varied so that the electrotransport agent delivery rate from the controller with one class of therapeutic agent sources is substantially different from the controller with another of said classes of therapeutic agent sources.

12. The device of claim 11, wherein said parameter is selected from the group consisting of therapeutic agent concentration, competitive co-ion concentration, skin contact area of the therapeutic agent source, pH of the therapeutic agent source, ion solvating property of a liquid solvent in the therapeutic agent source, flux enhancer content, and combinations thereof.

13. The device of claim 11, wherein each said therapeutic source comprises a drug reservoir having a pH.

14. The device of claim 13, wherein, within said plurality of classes of therapeutic agent sources, the pH of the drug reservoir is varied.

15. The device of claim 11, wherein each therapeutic agent source comprises a drug-containing unit having a drug-containing donor reservoir.

16. The device of claim 15, wherein each donor reservoir comprises multiple reservoir segments, each of said unit classes having a first portion of said reservoir segments containing drug and a second portion being substantially drug-free, and wherein the drug delivery rate is varied by varying, within said different classes, the ratio of drug-containing to drug-free reservoir segments.

17. The device of claim 16, wherein said second portion of reservoir segments contain a biocompatible electrolyte.

18. The device of claim 15, wherein said drug-containing units comprise a drug and competitive co-ions.

19. The device of claim 18, wherein said competitive co-ion concentration is provided by a secondary electrode in the drug-containing unit which generates competitive co-ions.

20. The device of claim 15, wherein the plurality of classes of drug-containing units each has different drug concentrations.

21. A method of delivering a therapeutic agent through a body surface from an electrotransport assembly of the type which includes a controller component and a detachable therapeutic agent source, the controller component operating at a predetermined, fixed electrical output, the method comprising the steps of:

provamting a plurality of therapeutic agent sources in which a single parameter or a series of parameters has been varied so that, in conjunction with said controller component, agent delivery rate can be selectively controlled by coupling and uncoupling said therapeutic agent sources to the controller component; and interchanging said agent sources whereby therapeutic agent delivery rate is selectively controlled at fixed controller-component electrical output.

22. An electrotransport delivery system comprising:

an electrotransport device for delivering a therapeutic agent through a body surface, the device including a controller which operates at a predetermined, substantially fixed electrical output, the controller being adapted to be detachably connected to a plurality of therapeutic agent sources; and a plurality of different therapeutic agent sources in which a parameter in each said different sources has been varied so that electrotransport agent delivery rate from the system with one of said sources is substantially different from the electrotransport agent delivery rate from the system with another of said sources.

23. A system according to claim 22, wherein the parameter of the therapeutic agent source is selected from the group consisting of therapeutic agent concentration, competitive co-ion concentration, skin contact area of therapeutic agent source, pH of the therapeutic agent source, ion solvating property of a liquid solvent in the therapeutic agent source, flux enhancer content, and combinations thereof.

24. A system according to claim 22, wherein each said therapeutic agent source comprises a drug reservoir having a pH.

25. A system according to claim 22, wherein each therapeutic agent source comprises a drug-containing unit having a drug-containing donor reservoir.

26. A system of claim 25, wherein each donor reservoir comprises multiple reservoir segments, a plurality of said reservoir segments containing drug and a plurality of said reservoir segments being substantially drug-free, and wherein the drug delivery rate of the system is varied by varying the ratio of drug-containing to drug-free reservoir segments.

27. The device of claim 26, wherein said drug-free reservoir segments contain a biocompatible electrolyte.

28. A system according to claim 22, wherein the plurality of different therapeutic agent sources each has different agent concentrations.

* * * * *